United States Patent
Engstrand

(10) Patent No.: US 9,182,342 B2
(45) Date of Patent: Nov. 10, 2015

(54) APPARATUS, SYSTEM AND METHOD FOR USING AN LED TO IDENTIFY A PRESENCE OF A MATERIAL IN A GAS AND/OR A FLUID AND/OR DETERMINE PROPERTIES OF THE MATERIAL

(75) Inventor: Bradley W. Engstrand, Hartford, WI (US)

(73) Assignee: MOTION CONTROLS, LLC, Hartford, WI (US)

( * ) Notice: Subject to any disclaimer, the term of this patent is extended or adjusted under 35 U.S.C. 154(b) by 1062 days.

(21) Appl. No.: 13/200,493

(22) Filed: Sep. 23, 2011

(65) Prior Publication Data
US 2013/0077097 A1 Mar. 28, 2013

(51) Int. Cl.
| | |
|---|---|
| G01N 21/31 | (2006.01) |
| G01N 21/41 | (2006.01) |
| G01N 21/45 | (2006.01) |
| G01N 21/53 | (2006.01) |
| G01N 21/47 | (2006.01) |
| G01N 21/51 | (2006.01) |

(52) U.S. Cl.
CPC .............. *G01N 21/31* (2013.01); *G01N 21/41* (2013.01); *G01N 21/45* (2013.01); *G01N 21/53* (2013.01); *G01N 2021/3181* (2013.01); *G01N 2021/4711* (2013.01); *G01N 2021/516* (2013.01); *G01N 2201/062* (2013.01)

(58) Field of Classification Search
USPC ................................................. 356/432–442
See application file for complete search history.

(56) References Cited

U.S. PATENT DOCUMENTS

| | | | | | |
|---|---|---|---|---|---|
| 3,586,862 | A | * | 6/1971 | Topol | 250/574 |
| 3,948,345 | A | * | 4/1976 | Rosencwaig | 73/579 |
| 4,042,304 | A | * | 8/1977 | Martin et al. | 356/128 |
| 4,214,161 | A | | 7/1980 | Talroze | |
| 4,661,695 | A | | 4/1987 | Mori et al. | |
| 4,777,359 | A | | 10/1988 | Havel | |
| 4,811,561 | A | | 3/1989 | Edwards et al. | |
| 4,818,348 | A | | 4/1989 | Stetter | |
| 4,868,546 | A | * | 9/1989 | Dumbeck | 340/632 |
| 4,902,903 | A | | 2/1990 | Segerson et al. | |
| 4,902,978 | A | | 2/1990 | Horigan | |
| 4,962,395 | A | | 10/1990 | Baird | |
| 5,184,009 | A | | 2/1993 | Wright | |
| 5,684,246 | A | | 11/1997 | Korpi | |
| 5,988,676 | A | | 11/1999 | Lotito | |

(Continued)

FOREIGN PATENT DOCUMENTS

WO PCT/US12/56933 12/2012

*Primary Examiner* — Gregory J Toatley
*Assistant Examiner* — Rebecca C Bryant
(74) *Attorney, Agent, or Firm* — Patents + TMS, P.C.

(57) ABSTRACT

An apparatus, a system and a method use a light-emitting diode (LED) to identify the presence of a material in a gas and/or a fluid and/or to determine properties of the material. The LED and a light detector may be used to determine a chemical compound in the material. The gas and/or the fluid may be located in a chamber. A first light detector may be positioned on the opposite side of the chamber relative to the LED, a second light detector may be positioned on the same side of the chamber as the LED, and/or a third light detector may be positioned inside the chamber. Additional light detectors with coatings may enable measurements to be corrected for the effects of temperature. The light detectors may determine light reflection, light refraction, light transmission, light diffraction, light interference, light diffusion, light collimation, light absorption and/or light focusing of the material.

17 Claims, 4 Drawing Sheets

(56) References Cited

U.S. PATENT DOCUMENTS

| | | | |
|---|---|---|---|
| 5,990,990 A | 11/1999 | Crabtree | |
| 6,115,168 A | 9/2000 | Zhao et al. | |
| 6,180,955 B1 | 1/2001 | Doggett et al. | |
| 6,315,955 B1 * | 11/2001 | Klein | 422/73 |
| 6,484,620 B2 | 11/2002 | Arshad et al. | |
| 6,600,144 B2 | 7/2003 | Matthies | |
| 6,611,318 B2 | 8/2003 | LaPolice | |
| 6,952,009 B1 | 10/2005 | Engstrand | |
| 7,157,294 B2 | 1/2007 | Uemura et al. | |
| 7,180,053 B2 | 2/2007 | Engstrand | |
| 7,291,830 B1 | 11/2007 | Engstrand | |
| 7,294,823 B2 | 11/2007 | Engstrand | |
| 7,348,542 B2 * | 3/2008 | Engstrand | 250/231.1 |
| 7,388,188 B2 | 6/2008 | Engstrand | |
| 7,456,385 B2 | 11/2008 | Engstrand | |
| 7,468,522 B2 | 12/2008 | Engstrand | |
| 7,476,842 B2 | 1/2009 | Engstrand | |
| 7,518,100 B2 | 4/2009 | Engstrand | |
| 7,626,153 B2 | 12/2009 | Engstrand | |
| 7,703,279 B2 | 4/2010 | Engstrand | |
| 7,935,916 B2 | 5/2011 | Engstrand | |
| 2002/0168153 A1 | 11/2002 | Yamabayashi et al. | |
| 2003/0043107 A1 | 3/2003 | Ruby et al. | |
| 2003/0105218 A1 | 6/2003 | Halladay | |
| 2004/0004717 A1 | 1/2004 | Reed | |
| 2004/0249579 A1 * | 12/2004 | Centanni | 702/25 |
| 2005/0170525 A1 | 8/2005 | Kuroda | |
| 2007/0115686 A1 | 5/2007 | Tyberghien | |
| 2008/0317089 A1 * | 12/2008 | Fontana et al. | 374/33 |

* cited by examiner

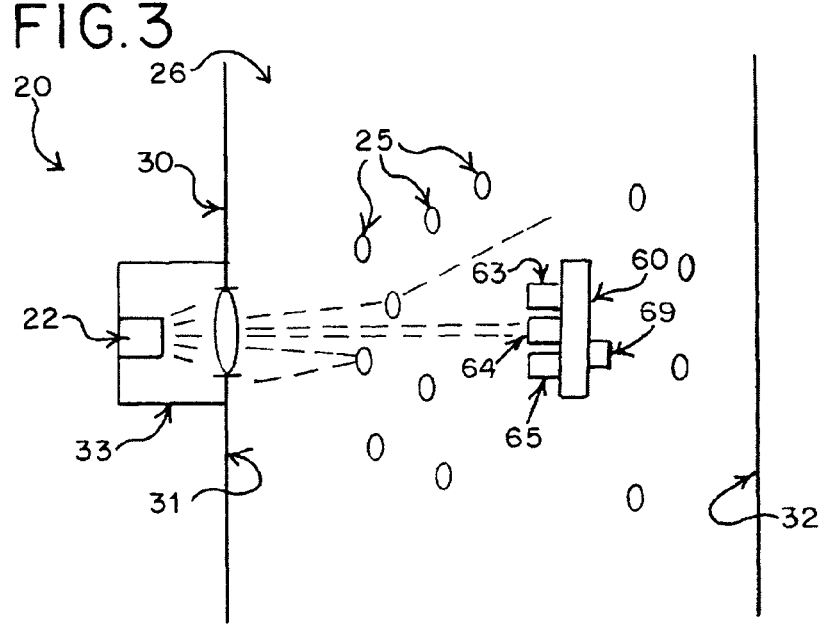
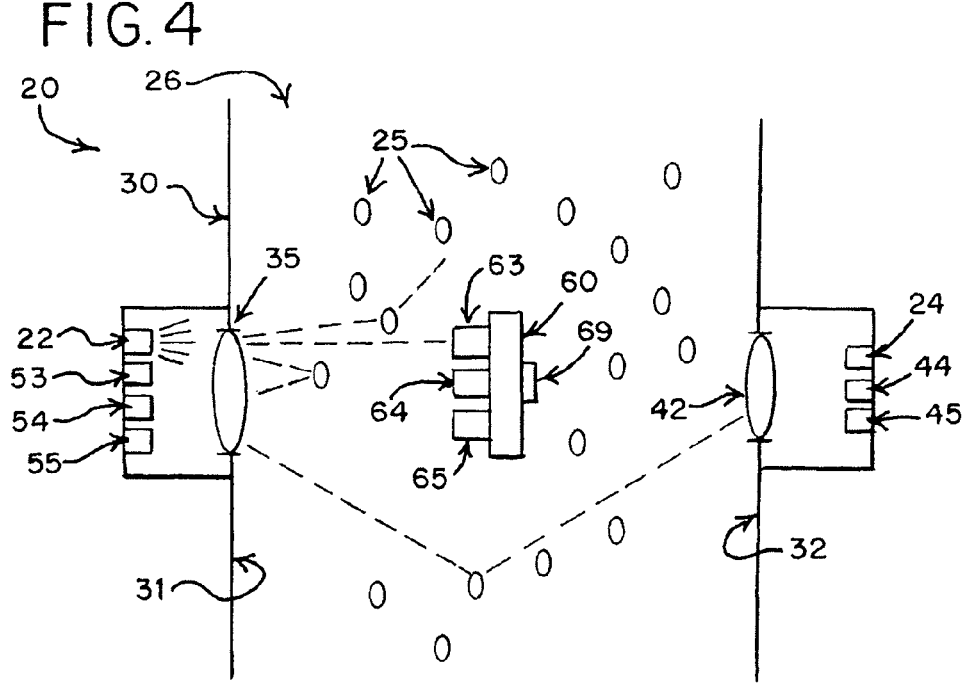

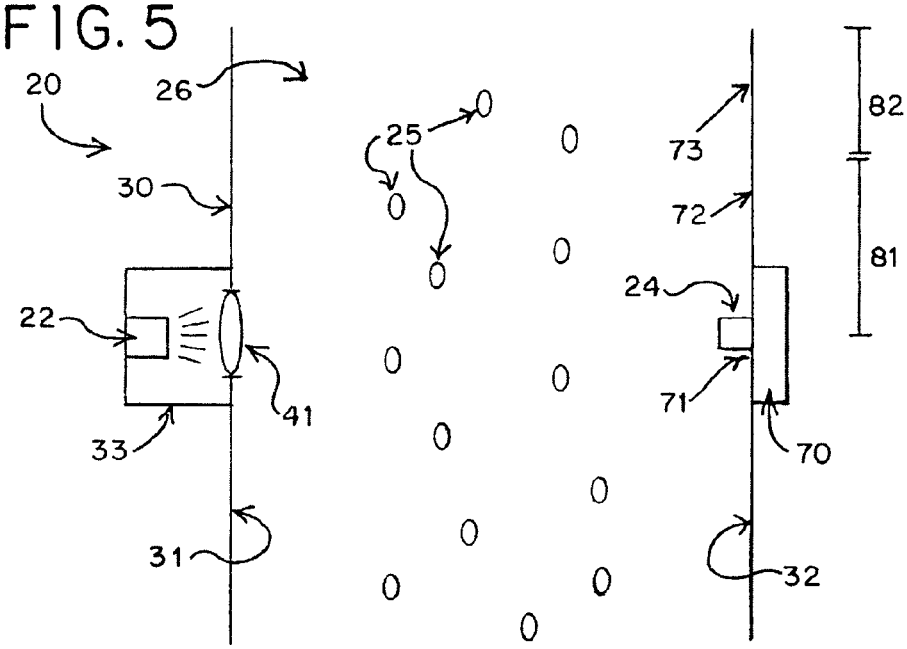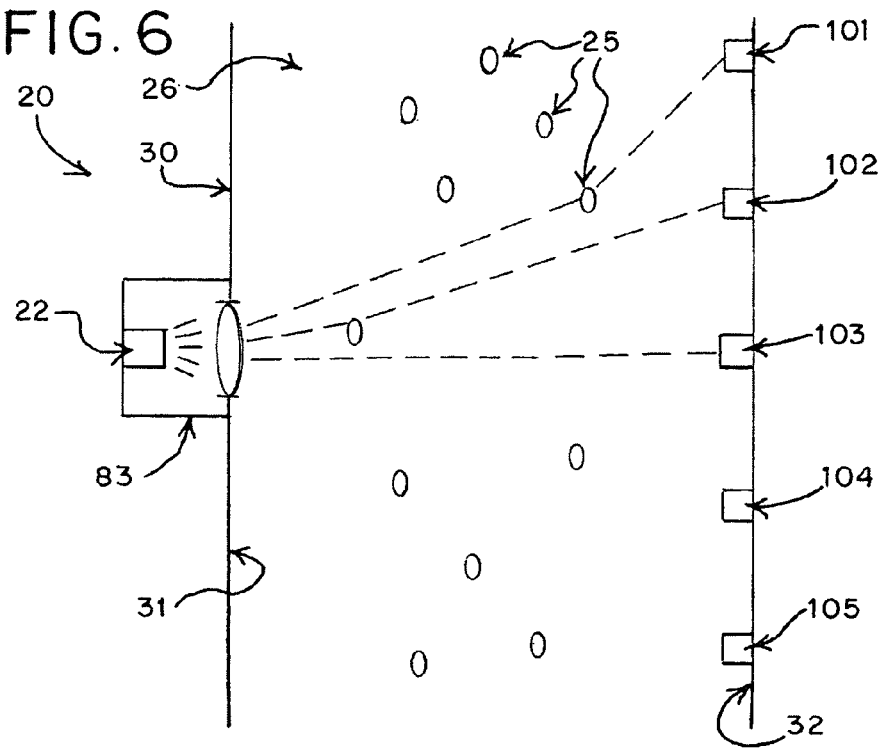

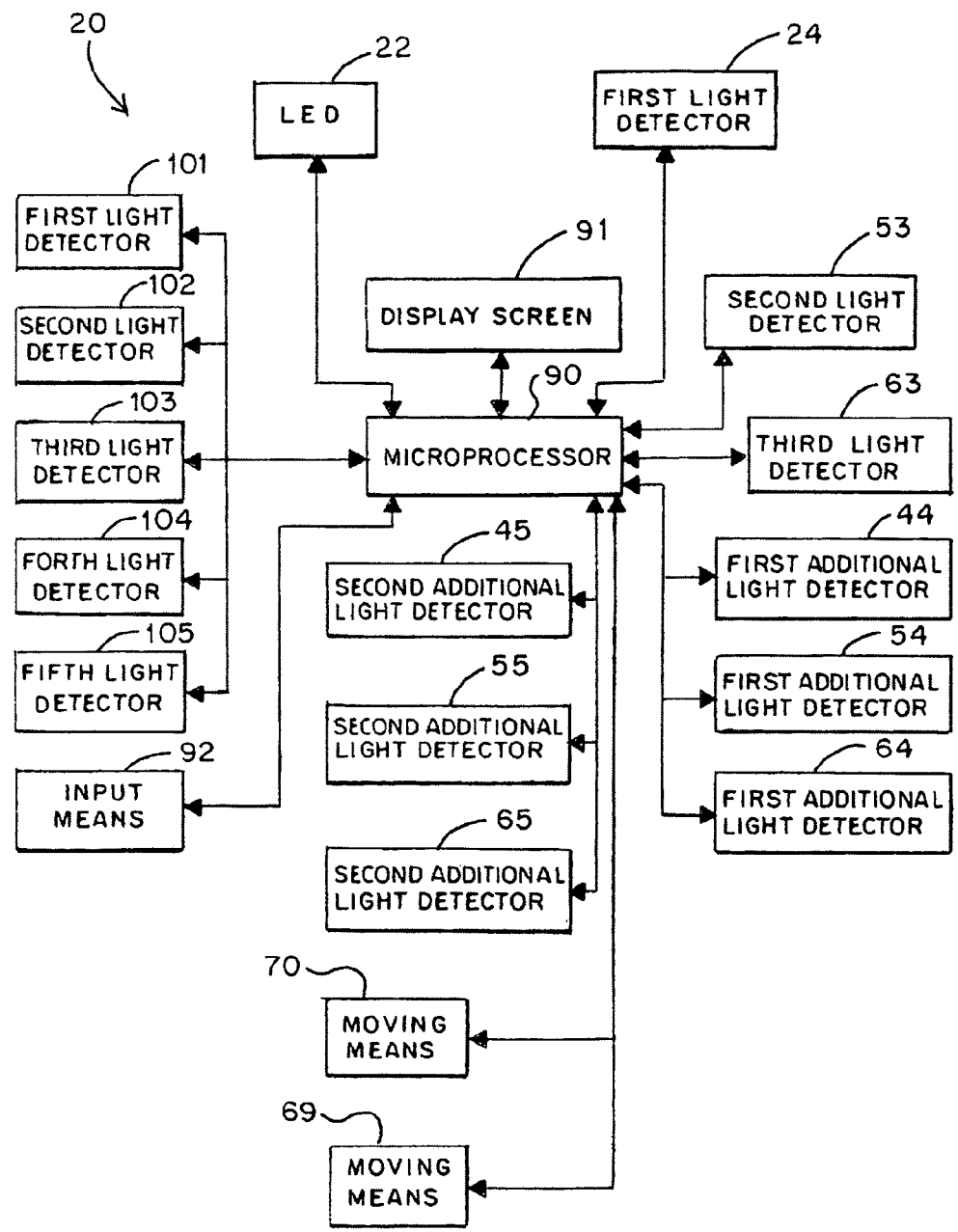

APPARATUS, SYSTEM AND METHOD FOR USING AN LED TO IDENTIFY A PRESENCE OF A MATERIAL IN A GAS AND/OR A FLUID AND/OR DETERMINE PROPERTIES OF THE MATERIAL

BACKGROUND OF THE INVENTION

The present invention generally relates to an apparatus, a system and a method for using a light-emitting diode (LED) to identify a presence of a material in a gas and/or a fluid and/or determine properties of the material. More specifically, the present invention relates to an LED and a light detector that may be used to determine the presence or absence of the material in the gas and/or the fluid and the properties of the material, such as a refractive index of the material and/or a chemical compound in the material.

The presence of a material in a fluid is important for slurries. A slurry is a suspension of solids in a liquid. An example of a commercially implemented slurry is an ethanol slurry made from the fermentation of corn or another starch. Ethanol slurries are used to produce fuels, alcoholic beverages, solvents, and organic reagents. The purity of the slurry may be critical for the subsequent uses of the slurry. It is known to detect irregularities in a slurry using ultrasonic testing. However, equipment to generate ultrasonic pulses for such testing is expensive. Therefore, ultrasonic testing of slurries is costly. Accordingly, a need exists for an apparatus, a system and a method for using an LED to identify a presence of irregularities in a slurry and determine the properties of the irregularities.

The presence of a material in a fluid is also important for transformers. A transformer is an electrical device that has a primary coil and a secondary coil. The primary coil accepts an input current, and travel of the input current through the primary coil generates a magnetic field that extends to the secondary coil. A change in the current in the primary coil causes changes in the magnetic field to which the secondary current is exposed, which induces a current in the secondary coil. As a result, a transformer converts power to a different voltage which is dependent on the number of turns in each of the coils.

Typically, mineral oil is used to insulate the transformer. More specifically, the coils of the transformer are immersed in a highly-refined mineral oil which is stable at high temperatures. However, gas bubbles or water in the mineral oil may cause arcing. Arcing is the electrical breakdown of gas caused by a current flowing through normally nonconductive media. Arcing may introduce carbon contaminants into the mineral oil of the transformer. Gas bubbles, water, and carbon contaminants may impair the ability of the mineral oil to insulate the transformer. Therefore, these irregularities may cause a transformer to overheat. Accordingly, a need exists for an apparatus, a system and a method for using an LED to identify a presence of irregularities in mineral oil insulating a transformer and determine the properties of the irregularities.

The presence of a material in a fluid is also important for aircraft engine oil, such as mineral oil or synthetic oil. Aircraft engine oil lubricates, cools, cleans, seals the components of the engine, protects against corrosion, and reduces noise. Without the lubrication provided by the oil, the moving parts of the aircraft engine directly contact each other and, as a result, degrade rapidly. Debris in aircraft engine oil may prevent the oil from providing lubrication and the other functions. For example, ceramic bearings are high performance bearings but are not used in aircraft engines because ceramic shards introduced into the aircraft engine oil cannot be detected using known oil turbidity sensors. Undetected ceramic shards may impair aircraft engine oil function and typically are not identified until engine trouble occurs. Therefore, lower performance bearings which create debris detected by known oil turbidity sensors are used in aircraft engines. Accordingly, a need exists for an apparatus, a system and a method for using an LED to identify a presence of ceramic in aircraft engine oil.

The presence of a material in a fluid is also important for central intravenous tubing, namely intravenous tubing which uses a catheter inserted into a large vein. Intravenous tubing may deliver an air bubble into the patient's circulation to block a vessel and cause an embolism. Peripheral intravenous tubing, namely intravenous tubing which uses a short catheter inserted into a peripheral vein, has a low risk of embolism because a large bubble cannot travel through a narrow catheter; however, a greater risk of air bubble-induced embolism is presented by central intravenous tubing. An embolism may cause life-threatening damage to pulmonary circulation or stop the heart. Accordingly, a need exists for an apparatus, a system and a method for using an LED to identify a presence of air bubbles in central intravenous tubing.

SUMMARY OF THE INVENTION

The present invention generally relates to an apparatus, a system and a method for using a light-emitting diode (LED) to identify a presence of a material in a gas and/or a fluid and/or determine properties of the material. More specifically, the present invention relates to an LED and a light detector that may be used to determine the presence or absence of the material in the gas and/or the fluid and the properties of the material, such as a refractive index of the material and/or a chemical compound in the material. The gas and/or the fluid may be located in a chamber. A first light detector may be positioned on the opposite side of the chamber relative to the LED, a second light detector may be positioned on the same side of the chamber as the LED, and/or a third light detector may be positioned inside the chamber.

To this end, in an embodiment of the present invention, a system for identifying a presence of a material in a medium is provided. The medium is at least one of a gas and a fluid. The system has a chamber in which the medium is located wherein the chamber has a first side and a second side and further wherein the first side is located in an opposite position relative to the second side. Further, the system has an LED to emit light wherein the LED is adjacent to the first side of the chamber. Still further, the system has a first light detector which detects an intensity of the light at a first position on the second side of the chamber wherein the first light detector is adjacent to the second side of the chamber and further wherein the first light detector produces a first signal indicative of the intensity of the light at the first position. Still further, the system has a second light detector which detects an intensity of the light at a second position on the first side of the chamber wherein the second light detector is adjacent to the first side of the chamber and further wherein the second light detector produces a second signal indicative of the intensity of the light at the second position. Moreover, the system has a third light detector which detects an intensity of the light at a third position within the chamber wherein the third light detector is within the chamber and further wherein the third light detector produces a third signal indicative of the intensity of the light at the third position. In addition, the system has a microprocessor communicatively connected to the first light detector, the second light detector and the third light detector wherein the microprocessor processes the first signal, the second signal and the third signal to determine whether the material is present in the medium.

In an embodiment, the system has a compartment in the first side of the chamber wherein the LED and the second light detector are located in the compartment.

In an embodiment, the system has a compartment in the second side of the chamber wherein the first light detector is located in the compartment.

In an embodiment, the system has a lens on the first side of the chamber wherein the chamber is located on an opposite side of the lens relative to the LED and the second light detector.

In an embodiment, the system has a lens on the second side of the chamber wherein the lens is located between the first light detector and the chamber.

In an embodiment, the system has moving means connected to the third light detector wherein the moving means moves the third light detector from a first position relative to the LED to a second position relative to the LED.

In an embodiment, the system has a display screen connected to the microprocessor wherein the display screen visually indicates whether the material is present in the medium.

In an embodiment, the system has input means connected to the microprocessor wherein user input accepted by the input means indicates a selected time and further wherein the microprocessor responds to the user input by indicating whether the material was present in the medium at the selected time.

In an embodiment, the system has an additional light detector located adjacent to one of the first light detector, the second light detector and the third light detector wherein the additional light detector has a coating of carbon black wherein the carbon black has a CAS Registry Number of 1333-86-4.

In an embodiment, the system has an additional light detector located adjacent to one of the first light detector, the second light detector and the third light detector wherein the additional light detector has a coating of titanium dioxide.

In another embodiment of the present invention, a method for identifying a presence of a material in a medium is provided. The medium is at least one of a gas and a fluid, and the medium is located in a chamber having a first side and a second side. The first side is located in an opposite position relative to the second side. The method has the steps of emitting light from an LED which is adjacent to the first side of the chamber; detecting an intensity of the light at a first position relative to the LED; transmitting the intensity of the light at the first position to a microprocessor; and using the intensity of the light at the first position to determine whether the material is present in the medium wherein the microprocessor determines whether the material is present in the medium.

In an embodiment, the method has the step of using the intensity of the light at the first position to determine a refractive index of the material wherein the microprocessor determines the refractive index of the material.

In an embodiment, the method has the step of using the intensity of the light at the first position to determine light transmission of the material wherein the microprocessor determines the light transmission of the material.

In an embodiment, the first position is located on the first side of the chamber.

In an embodiment, the first position is located on the second side of the chamber.

In an embodiment, the first position is located within the chamber.

In an embodiment, the method has the step of detecting an intensity of the light at a second position relative to the LED wherein the second position is a different position than the first position and further wherein the microprocessor uses the intensity of the light at the first position and the intensity of the light at the second position to determine whether the material is present in the medium.

In another embodiment of the present invention, an apparatus for identifying a presence of a material in a medium is provided. The medium is at least one of a gas and a fluid. The apparatus has a chamber in which the medium is located wherein the chamber has a first side and a second side and further wherein the first side is located in an opposite position relative to the second side. Further, the apparatus has an LED to emit light wherein the LED is adjacent to the first side of the chamber. Still further, the apparatus has a first light detector which detects an intensity of the light at a first position on the second side of the chamber wherein the first light detector is adjacent to the second side of the chamber. Moreover, the apparatus has a microprocessor communicatively connected to the first light detector wherein the microprocessor uses the intensity of the light at the first position to determine whether the material is present in the medium.

In an embodiment, the apparatus has a second light detector adjacent to the second side of the chamber wherein the second light detector detects an intensity of the light at a second position on the second side of the chamber and further wherein the second position is a different position relative to the LED than the first position wherein the microprocessor uses the intensity of the light at the first position and the intensity of the light at the second position to determine whether the material is present in the medium.

In an embodiment, the apparatus has moving means connected to the first light detector wherein the moving means moves the first light detector from the first position on the second side of the chamber to a second position on the second side of the chamber.

It is, therefore, an advantage of the present invention to provide an apparatus, a system and a method for using an LED to identify a presence of a material in a gas and/or a fluid.

Another advantage of the present invention is to provide an apparatus, a system and a method for using an LED to determine properties of a material in a gas and/or a fluid.

Further, an advantage of the present invention is to provide an apparatus, a system and a method for using an LED to identify a presence of a material in a gas and/or a fluid which use an intensity of light to determine the properties of the material.

Yet another advantage of the present invention is to provide an apparatus, a system and a method for using an LED to identify a presence of a material in a gas and/or a fluid which determine light reflection, light refraction, light transmission, light diffraction and/or light interference of the material.

In addition, an advantage of the present invention is to provide an apparatus, a system and a method for using an LED to identify a presence of a material in a gas and/or a fluid which do not use ultrasonic pulses.

Another advantage of the present invention is to provide an apparatus, a system and a method for using a LED to identify a presence of irregularities in a slurry and determine the properties of the irregularities.

Still further, an advantage of the present invention is to provide an apparatus, a system and a method for using an LED to identify a presence of irregularities in mineral oil insulating a transformer and determine the properties of the irregularities.

Yet another advantage of the present invention is to provide an apparatus, a system and a method for using an LED to identify a presence of ceramic in aircraft engine oil.

In addition, an advantage of the present invention is to provide an apparatus, a system and a method for using an LED to identify a presence of air bubbles in central intravenous tubing.

Another advantage of the present invention is to provide an apparatus, a system and a method for using an LED to identify a presence of a material in a gas and/or a fluid which correct for effects of temperature.

Moreover, an advantage of the present invention is to provide an apparatus, a system and a method for using an LED to identify a presence of a material in a gas and/or a fluid which may be used at any temperature.

Yet another advantage of the present invention is to provide an apparatus, a system and a method for using an LED to identify a presence of a material in a gas and/or a fluid which may use multiple frequencies of light.

In addition, an advantage of the present invention is to provide an apparatus, a system and a method for using an LED to identify a presence of a material in a gas and/or a fluid which use light detectors located in various positions.

Another advantage of the present invention is to provide an apparatus, a system and a method for using an LED to identify a presence of a material in a gas and/or a fluid which use a light detector which moves from a first position to a second position relative to the LED.

Moreover, an advantage of the present invention is to provide an apparatus, a system and a method for using an LED and a light detector to identify a presence of a material in a gas and/or a fluid which provide time-stamped data for light measurements obtained by the light detector.

Yet another advantage of the present invention is to provide an apparatus, a system and a method for using an LED to identify a presence of a material in a gas and/or a fluid which detect advanced properties of the material, such as light diffusion, light collimation, light absorption and/or light focusing.

In addition, an advantage of the present invention is to provide an apparatus, a system and a method for using an LED to identify a presence of a material in a gas and/or a fluid which use light detectors located at various positions relative to the LED.

Additional features and advantages of the present invention are described in, and will be apparent from, the detailed description of the presently preferred embodiments and from the drawings.

BRIEF DESCRIPTION OF THE DRAWINGS

FIGS. 1-6 illustrate side views of systems for using an LED to identify the presence of a material in a gas and/or a fluid and/or determine properties of the material in embodiments of the present invention.

FIG. 7 illustrates a box diagram of a system for using an LED to identify the presence of a material in a gas and/or a fluid and/or determine properties of the material in an embodiment of the present invention.

DETAILED DESCRIPTION OF THE PRESENTLY PREFERRED EMBODIMENTS

The present invention generally relates to an apparatus, a system and a method for using a light-emitting diode (LED) to identify a presence of a material in a gas and/or a fluid and/or determine properties of the material. More specifically, the present invention relates to an LED and a light detector that may be used to determine the presence or absence of the material in the gas and/or the fluid and the properties of the material, such as, for example, a refractive index of the material and/or a chemical compound in the material.

The gas and/or the fluid may be located in a chamber. A first light detector may be positioned on the opposite side of the chamber relative to the LED, a second light detector may be positioned on the same side of the chamber as the LED, and/or a third light detector may be positioned inside the chamber. One or more of the light detectors may be coupled to a first additional light detector having a carbon black coating. One or more of the light detectors may be coupled to a second additional light detector having a titanium dioxide coating. The first additional light detector and/or the second additional light detector may enable measurements to be corrected for the effects of temperature.

The light detectors may determine light reflection, light refraction, light transmission, light diffraction, light interference, light diffusion, light collimation, light absorption and/or light focusing of the material. One or more of these properties may be used to determine a chemical compound in the material.

Figure 1:
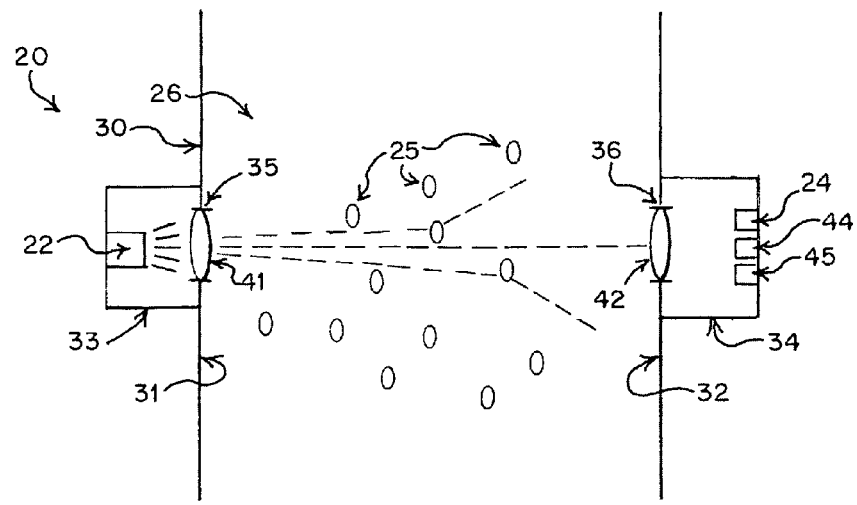

Referring now to the drawings wherein like numerals refer to like parts, FIG. 1 generally illustrates an embodiment of a system 20 for using an LED 22 to identify the presence of a material 25 in a gas and/or a fluid 26 and/or to determine properties of the material 25. The gas and/or the fluid 26 may be located in and/or may travel through a chamber 30. The gas and/or the fluid 26 may be, for example, a slurry, mineral oil, synthetic oil and/or medication being delivered through intravenous tubing. The gas and/or the fluid 26 may be any gas and/or any fluid, and the present invention is not limited to a specific embodiment of the gas and/or the fluid 26.

The chamber 30 may have a first side 31 and a second side 32, and the second side 32 may be located in a position opposite to the first side 31. In an embodiment, the chamber 30 may have a first opening (not shown) through which the gas and/or the fluid 26 enters the chamber 30 and may have a second opening (not shown) through which the gas and/or the fluid 26 exit the chamber 30. The first opening and the second opening may be the same opening or may be different openings. The chamber 30 may be stationary and/or may be moving. For example, in an embodiment, the chamber 30 may be a rotating pipe. As another example, the chamber 30 may be intravenous tubing. As yet another, the chamber 30 may be a conduit through which oil flows. The present invention is not limited to a specific embodiment of the chamber 30, and the chamber 30 may be any structure in which the gas and/or the fluid 26 may be located.

The LED 22 may be located adjacent to the first side 31 of the chamber 30. The LED 22 may emit one or more colors of light, such as, for example, blue light, red light, green light, white light and/or the like. The LED 22 may emit one or more types of light, such as, for example, infrared light, visible light, ultraviolet ("UV") light and/or the like. The present invention is limited to a specific embodiment of the LED 22. The LED 22 may be any light source known to one having ordinary skill in the art.

The LED 22 may have a finish (not shown) which may prevent and/or reduce reflection of ambient light from the LED 22 and/or may allow the light emitted from the LED 22 to pass through the finish. The finish may be produced by mechanically abrading and/or chemically altering the LED 22. In an embodiment, the finish may be a coating, such as, for example, one or more filters and/or chemicals placed over the LED 22.

In an embodiment, the LED 22 may be located in a first compartment 33 which may be connected to the chamber 30. The first compartment 33 may be a component of and/or may be mechanically connected to the chamber 30. The first compartment 33 may have access to the chamber 30 through a first aperture 35. The light emitted from the LED 22 may travel from the first compartment 33 into the chamber 30 through the first aperture 35. A first lens 41 may be located at least partially within the first aperture 35. The first lens 41 may be located between the LED 22 and the chamber 30. In an embodiment, the first lens 41 may be located between the LED 22 and the fluid and/or the gas 26.

The first lens 41 may focus the light emitted from the LED 22 into the fluid and/or the gas 26 located in the chamber 30. The first lens 41 may be, for example, a spherical ball lens, a fiber coupling sphere, a collimating lens and/or the like. Further, the first lens 41 may have a cross-sectional shape of a circle, an oval and/or the like, for example. In an embodiment, the first lens 41 may be made from glass. The first lens 41 may be made from any material, and the present invention is not limited to a specific embodiment of the first lens 41.

The light emitted from the LED 22 may travel through the gas and/or the fluid 26. The system 20 may have a first light detector 24 which may be, for example, a light intensity detector, a photodiode, a phototransistor and/or other like detector that may output a signal as a function of light intensity detected. In an embodiment, the signal may be a current and/or a voltage. The present invention is not limited to a specific embodiment of the first light detector 24 or the signal. The first light detector 24 may be any detector which measures an intensity of light known to one having ordinary skill in the art, and the signal may be any means of indicating the light intensity detected known to one having ordinary skill in the art.

The first light detector 24 may be located adjacent to the second side 32 of the chamber 30. The first light detector 24 may read and/or may measure an intensity of light which travels from the first side 31 through the fluid and/or the gas 26 to the second side 32 of the chamber 30.

If the material 25 is present in the gas and/or the fluid 26, the material 25 may reflect and/or may refract the light. As known to one having ordinary skill in the art, light reflection and light refraction are changes in the direction of travel of the light which occur if the light travels from a first medium to a second medium having a different refractive index (n) relative to the first medium. For reflection, the angle of incidence and angle of reflection are equal. For refraction, the angle of incidence and angle of reflection are not equal. Typically, when light contacts the second medium, a portion of the light reflects, and the remainder of the light refracts.

By measuring the angle of incidence and angle of refraction, the refractive index (n) of the material 25 may be determined. If the material 25 is more dense relative to the fluid and/or the gas 26, the refractive index (n) may be calculated using the equation n=sin i/sin r where sin i is the angle of incidence and sin r is the angle of refraction. If the material 25 is less dense relative to the fluid and/or the gas 26, the refractive index (n) may be calculated using the equation n=sin r/sin i where sin i is the angle of incidence and sin r is the angle of refraction.

The material 25 may have a different refractive index relative to the gas and/or the fluid 26. As a result, the material 25 may reflect and/or may refract the light emitted into the gas and/or the fluid 26 by the LED 22. Moreover, the material 25 may diffract the light emitted into the gas and/or the fluid 26 by the LED 22. As known to one having ordinary skill in the art, diffraction is the bending of the path of travel of light as the light travels adjacent to the edge of an object. The first light detector 24 may detect light which is not reflected, not refracted and/or not diffracted by the material 25.

An amount of the light detected by the first light detector 24 relative to an amount of the light emitted by the LED 22 may indicate an absence or a presence of the material 25. For example, if the ratio of the amount of the light detected by the first light detector 24 to the amount of the light emitted by the LED 22 is below a predetermined threshold for one or more wavelengths of light, the material 25 may be present. In embodiments of the present invention, the ratio of the amount of the light detected by the first light detector 24 to the amount of the light emitted by the LED 22 may indicate the presence or the absence of irregularities in a slurry, debris in oil, and/or bubbles in central intravenous tubing.

An amount of the light detected by the first light detector 24 relative to an amount of the light emitted by the LED 22 may be used to identify properties of the material 25. Different chemical compounds typically have different refractive indexes, and a specific chemical compound typically has a different refractive index for different wavelengths of light. Therefore, an amount of the light detected by the first light detector 24 at various wavelengths of light relative to an amount of the light of each wavelength emitted by the LED 22 may be used to identify properties of the material 25. For example, the refractive index of the material 25, the light transmission of the material 25, and/or the like may be determined using this ratio. The refractive indexes of the material 25 for the various wavelengths may be used to identify the identity of the material 25.

For example, a portion of IR light may travel through ceramic, and visible light may not travel through ceramic. A portion of IR light may travel through carbon, and visible light may not travel through carbon. Therefore, if the LED 22 emits IR light and visible light and the first light detector 24 detects a portion of the IR light and does not detect the visible light, the material 25 may be have ceramic and/or carbon. Moreover, the portion of IR light which travels through carbon is typically a larger portion than the portion of IR light which travels through ceramics. Therefore, the amount of IR light detected by the first light detector 24 relative to the amount of IR light emitted by the LED 22 may indicate whether the material 25 may be carbon or may be ceramic. More generally, the amount of the light detected by the first light detector 24 at various wavelengths of light relative to the amount of the light of each wavelength emitted by the LED 22 may be used to identify the identity of a chemical compound in the material 25.

In an embodiment, the first light detector 24 may be located in a second compartment 34 which may be connected to the chamber 30. The second compartment 34 may be a component of and/or may be mechanically connected to the chamber 30. The second compartment 34 may have access to the chamber 30 through a second aperture 36. The light emitted from the LED 22 may travel through the second aperture 36 into the second compartment 34 after traveling through the fluid and/or the gas 26. A second lens 42 may be located at least partially within the second aperture 36. The second lens 42 may be located between the first light detector 24 and the chamber 30. In an embodiment, the second lens 42 may be located between the first light detector 24 and the fluid and/or the gas 26. Alternatively, the first light detector 24 may be located at least partially within the chamber 30.

The light emitted from the LED 22 through the fluid and/or the gas 26 may be focused by the second lens 42 into the second compartment 34. The second lens 42 may be, for example, a spherical ball lens, a fiber coupling sphere, a collimating lens and/or the like. Further, the second lens 42 may have a cross-sectional shape of a circle, an oval and/or the like, for example. In an embodiment, the second lens 42 may be made from glass. The second lens 42 may be made from any material, and the present invention is not limited to a specific embodiment of the second lens 42.

A first additional light detector 44 and/or a second additional light detector 45 may be located adjacent to the first light detector 24. In an embodiment, the first additional light detector 44 and/or the second additional light detector 45 may be located in the second compartment 34. The first additional light detector 44 may have a carbon black coating. Carbon black is virtually pure elemental carbon in the form of colloidal particles produced by incomplete combustion or thermal decomposition of gaseous or liquid hydrocarbons under controlled conditions. CAS Registry Numbers are unique numerical identifiers assigned by the "Chemical Abstracts Service" to every chemical described in open scientific literature; the CAS Registry Number for carbon black is 1333-86-4.

The first additional light detector 44 and/or the second additional light detector 45 may be, for example, a light intensity detector, a photodiode, a phototransistor and/or other like detector that may output a signal as a function of light intensity detected. In an embodiment, the signal may be a current and/or a voltage. The present invention is not limited to a specific embodiment of the first additional light detector 44, the second additional light detector 45 or the signals. The first additional light detector 44 and the second additional light detector 45 may be any detector which measures an intensity of light known to one having ordinary skill in the art, and the signal may be any means of indicating the light intensity detected known to one having ordinary skill in the art.

High temperatures may cause the first light detector 24 to provide incorrect measurements of the light intensity. For example, high temperatures may cause the first light detector 24 to provide a signal which indicates a higher level of light intensity relative to the actual light intensity experienced by the first light detector 24. More specifically, higher temperatures may cause the first light detector 24 to generate an amount of current and/or voltage which does not correspond to the actual light intensity experienced by the first light detector 24.

However, white light may not travel through the carbon black coating. As a result, the signal provided by the first additional light detector 44 in response to the LED 22 emitting white light may indicate the effect of temperature. For example, the first light detector 24 may obtain a signal in response to the LED 22 emitting white light at a specific temperature. The first additional light detector 44 may obtain a signal in response to the LED 22 emitting white light at the specific temperature. The signal from the first additional light detector 44 may be subtracted from the signal from the first light detector 24 to correct for the effects of the specific temperature. Different wavelengths of white light may be emitted by the LED 22, and the effects of temperature may be corrected at each wavelength by subtracting the signal of the first additional light detector 44 from the signal of the first light detector 24 for the specific wavelength and the specific temperature.

As shown in FIG. 7, a microprocessor 90 may be communicatively connected to the first light detector 24 and/or the first additional light detector 44. The microprocessor 90 may subtract the signal provided by the first additional light detector 44 from the signal provided by the first light detector 24 at the specific temperature to obtain a signal corrected for the effect of the specific temperature. The microprocessor 90 may correct for the effects of temperature at different wavelengths. For example, for each wavelength and/or each temperature, the microprocessor 90 may subtract the signal of the first additional light detector 44 from the signal of the first light detector 24.

Referring again to FIG. 1, the second additional light detector 45 may have a titanium dioxide ($TiO_2$) coating. UV light is absorbed by titanium dioxide, and, as a result, UV light may not travel through the titanium dioxide coating on the second additional light detector 45. Therefore, the signal provided by the second additional light detector 45 in response to the LED 22 emitting UV light may indicate the effect of temperature. For example, the first light detector 24 may obtain a signal in response to the LED 22 emitting UV light at a specific temperature. The second additional light detector 45 may obtain a signal in response to the LED 22 emitting UV light at the specific temperature. The signal from the second additional light detector 45 may be subtracted from the signal from the first light detector 24 to correct for the effect of the specific temperature. Different wavelengths of UV light may be emitted by the LED 22, and the effects of temperature may be corrected at each wavelength by subtracting the signal from the second additional light detector 45 from the signal from the first light detector 24 for the specific wavelength and the specific temperature.

As shown in FIG. 7, the microprocessor 90 may be communicatively connected to the first light detector 24 and/or the second additional light detector 45. The microprocessor 90 may subtract the signal provided by the second additional light detector 45 from the signal provided by the first light detector 24 at the specific temperature to obtain a signal corrected for the effect of the specific temperature. For example, for each wavelength and/or each temperature, the microprocessor 90 may subtract the signal of the second additional light detector 45 from the signal of the first light detector 24.

Figure 2:
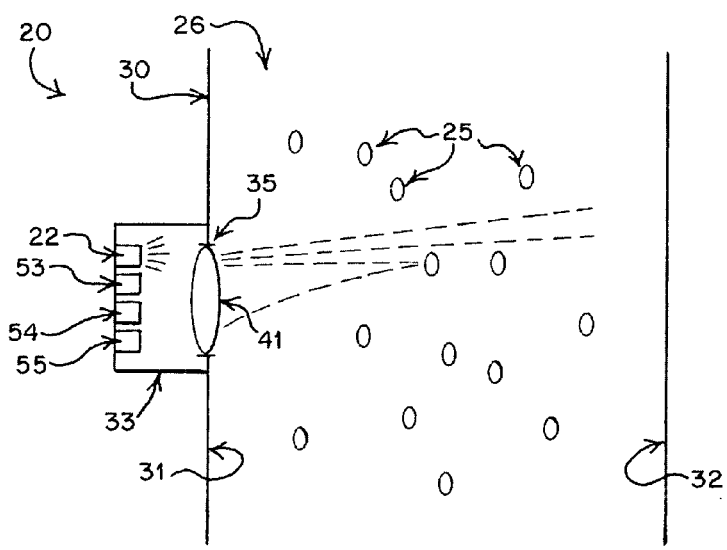

FIG. 2 generally illustrates an embodiment of the system 20 for using the LED 22 to identify the presence of the material 25 in the gas and/or the fluid 26 and/or to determine properties of the material 25. In this embodiment, a second light detector 53 may be located adjacent to the first side 31 of the chamber 30. For example, the second light detector 53 may be located in the first compartment 33. An amount of the light detected by the second light detector 53 relative to an amount of the light emitted by the LED 22 may be used to identify the absence or the presence of the material 25. For example, if the ratio of the amount of the light detected by the second light detector 53 to the amount of the light emitted by the LED 22 exceeds a predetermined threshold for one or more wavelengths, the material 25 may be present in the gas and/or the fluid 26. In embodiments of the present invention, the ratio of the amount of the light detected by the second light detector 53 to the amount of the light emitted by the LED 22 may indicate irregularities in a slurry, debris in oil, and/or bubbles in central intravenous tubing.

Moreover, as previously set forth, different materials typically have different refractive indexes, and a specific material chemical compound typically has a different refractive index for different wavelengths of light. Therefore, an amount of the light detected by the first light detector 24 at various wavelengths of light relative to an amount of the light of each wavelength emitted by the LED 22 may be used to identify properties of the material 25. For example, the refractive index of the material 25, the light transmission of the material 25, and/or the like may be identified using the ratio. The refractive indexes of the material 25 for the various wavelengths may be used to identify the identity of a chemical compound in the material 25. For example, ceramics may reflect a larger portion of the light emitted from the LED 22 relative to carbon. Accordingly, the amount of the light detected by the first light detector 24 at various wavelengths of light relative to the amount of the light of each wavelength emitted by the LED 22 may be used to identify the identity of a chemical compound in the material 25.

A first additional light detector 54 and/or a second additional light detector 55 may be located adjacent to the second light detector 53. In an embodiment, the first additional light detector 54 and/or the second additional light detector 55 may be located in the first compartment 33. The first additional light detector 54 may have a carbon black coating, and/or the second additional light detector 45 may have a titanium dioxide ($TiO_2$) coating. As previously set forth, white light may not travel through a carbon black coating. As a result, the signal provided by the first additional light detector 54 in response to the LED 22 emitting white light may indicate the effect of temperature. Different wavelengths of light may be emitted by the LED 22, and the effects of temperature may be corrected at each wavelength by subtracting the signal of the first additional light detector 54 from the signal of the second light detector 53 for the specific wavelength and the specific temperature.

As shown in FIG. 7, the microprocessor 90 may be communicatively connected to the first light detector 24 and/or the first additional light detector 54. The microprocessor 90 may subtract the signal provided by the first additional light detector 54 at a specific temperature from the signal provided by the first light detector 24 at the specific temperature to obtain a signal corrected for the effect of the specific temperature. For example, for each wavelength and/or each temperature, the microprocessor 90 may subtract the signal of the first additional light detector 54 from the signal of the second light detector 53.

As previously set forth, UV light may not travel through a titanium dioxide coating. Therefore, the signal provided by the second additional light detector 55 in response to the LED 22 emitting UV light may indicate the effect of temperature. As shown in FIG. 7, the microprocessor 90 may be communicatively connected to the second light detector 53 and/or the second additional light detector 55. The microprocessor 90 may subtract the signal provided by the second additional light detector 55 at a specific temperature from the signal provided by the second light detector 53 at the specific temperature to obtain a signal corrected for the effect of the specific temperature.

The second light detector 53, the first additional light detector 54 and/or the second additional light detector 55 may be, for example, a light intensity detector, a photodiode, a phototransistor and/or other like detector that may output a signal as a function of light intensity detected. In an embodiment, the signal may be a current and/or a voltage. The present invention is not limited to a specific embodiment of the second light detector 53, the first additional light detector 54 and/or the second additional light detector 55 or the signals. The second light detector 53, the first additional light detector 54 and/or the second additional light detector 55 may be any detector which measures an intensity of light known to one having ordinary skill in the art, and the signals may be any means of indicating the light intensity detected known to one having ordinary skill in the art.

FIG. 3 generally illustrates an embodiment of the system 20 for using the LED 22 to identify the presence of the material 25 in the gas and/or the fluid 26 and/or to determine properties of the material 25. In this embodiment, a third light detector 63 may be located between the first side 31 and the second side 32 of the chamber 30. For example, the third light detector 63 may be located in the chamber 30 and/or in the gas and/or the fluid 26. The third light detector 63 may be mechanically connected to a platform 60 which may be suspended within the chamber 30 and/or within the gas and/or the fluid 26.

As previously set forth, if the material 25 is present in the gas and/or the fluid 26, the material 25 may reflect, may refract and/or may diffract the light emitted into the gas and/or the fluid 26 by the LED 22. The third light detector 63 may detect the light not reflected, not refracted and/or not diffracted by the material 25 in a direction away from the third light detector 63. An amount of the light detected by the third light detector 63 relative to the amount of the light emitted by the LED 22 may indicate an absence or a presence of the material 25. For example, if the ratio of the amount of the light detected by the third light detector 63 to the amount of the light emitted by the LED 22 is below a predetermined threshold for one or more wavelengths, the material 25 may be present. In embodiments of the present invention, the ratio of the amount of the light detected by the third light detector 63 to the amount of the light emitted by the LED 22 may indicate irregularities in a slurry, debris in oil, and/or bubbles in central intravenous tubing.

A first additional light detector 64 and/or a second additional light detector 65 may be located adjacent to the third light detector 63. In an embodiment, the first additional light detector 64 and/or the second additional light detector 65 may be mechanically connected to the platform 60. The first additional light detector 64 may have a carbon black coating, and/or the second additional light detector 65 may have a titanium dioxide ($TiO_2$) coating. As previously set forth, white light may not travel through a carbon black coating. As a result, the signal provided by the first additional light detector 64 in response to the LED 22 emitting white light may indicate the effect of temperature. Different wavelengths of light may be emitted by the LED 22, and the effects of temperature may be corrected at each wavelength by subtracting the signal of the first additional light detector 64 from the signal of the third light detector 63 for the specific wavelength and the specific temperature.

As shown in FIG. 7, the microprocessor 90 may be communicatively connected to the third light detector 63 and/or the first additional light detector 64. The microprocessor 90 may subtract the signal provided by the first additional light detector 64 at a specific temperature from the signal provided by the third light detector 63 at the specific temperature to obtain a signal corrected for the effect of the specific temperature. For example, for each wavelength and/or each temperature, the microprocessor 90 may subtract the signal of the first additional light detector 64 from the signal of the third light detector 63.

As previously set forth, UV light may not travel through a titanium dioxide coating. Therefore, the signal provided by the second additional light detector 65 in response to the LED 22 emitting UV light may indicate the effect of temperature. As shown in FIG. 7, the microprocessor 90 may be communicatively connected to the third light detector 63 and/or the second additional light detector 65. The microprocessor 90 may subtract the signal provided by the second additional light detector 65 at a specific temperature from the signal provided by the third light detector 63 at the specific temperature to obtain a signal corrected for the effect of the specific temperature. For example, for each wavelength and/or each temperature, the microprocessor 90 may subtract the signal of the second additional light detector 65 from the signal of the third light detector 63.

The third light detector 63, the first additional light detector 64 and/or the second additional light detector 65 may be, for example, a light intensity detector, a photodiode, a phototransistor and/or other like detector that may output a signal as a function of light intensity detected. In an embodiment, the signal may be a current and/or a voltage. The present invention is not limited to a specific embodiment of the third light detector 63, the first additional light detector 64 and/or the second additional light detector 65 or the signals. The third light detector 63, the first additional light detector 64 and/or the second additional light detector 65 may be any detector which measures an intensity of light known to one having ordinary skill in the art, and the signals may be any means of indicating the light intensity detected known to one having ordinary skill in the art.

Referring again to FIG. 3, in an embodiment, the platform 60 may be movable with respect to the chamber 30. The platform 60 may move from a first position within the chamber 30 to a second position within the chamber 30. Accordingly, the third light detector 64, the first additional light detector 65 and/or the second additional light detector 65 may be moved from a first position to a second position within chamber 30. For example, the platform 60 may be moved closer to the LED 22, farther away from the LED 22, to a different angle relative to the LED 22, and/or the like. As a result, the third light detector 64 may be moved closer to the LED 22, farther away from the LED 22, to a different angle relative to the LED 22, and/or the like. Such movement of the third light detector 64 may enable the light emitted from the LED 22 to travel through less of the gas and/or the fluid 26 before reaching the third light detector 64, through more of the gas and/or the fluid 26 before reaching the third light detector 64, and/or at a different angle through the gas and/or fluid to reach the third light detector 64.

The system 20 may have a moving means 69 which may be activated and/or may be controlled by the microprocessor 90 to move the platform 60 and/or the third light detector 64. The moving means 69 may be, for example, a cable connected to the platform 60 and/or the third light detector 64, an extension which connects the chamber to the platform 60 and/or the third light detector 64 so that movement of the extension moves the platform 60 and/or the third light detector 64, and/or the like. The present invention is not limited to a specific embodiment of the moving means 69, and the moving means 69 may be any component of the system 20 which moves the platform 60 relative to the LED 22.

Moreover, as previously set forth, different materials typically have different refractive indexes, and a specific material typically has a different refractive index for different wavelengths of light. Therefore, an amount of the light detected by the third light detector 64 relative to an amount of the light emitted by the LED 22 for various wavelengths of light and/or various positions of the third light detector 64 may be used to identify properties of the material 25. For example, the refractive index of the material 25, the light transmission of the material 25, and/or the like may be determined. The refractive indexes of the material 25 for the various wavelengths and/or the various positions of the third light detector 64 may be used to identify the identity of a chemical compound in the material 25.

As shown in FIG. 4, an embodiment of the system 20 may have the first light detector 24, the second light detector 53 and the third light detector 63. The first light detector 24, the second light detector 53 and the third light detector 63 may provide light intensity measurements from various positions simultaneously. The light intensity measurements from various positions may improve calculations of the properties of the material 25, such as the refractive index of the material 25, for example. However, embodiments of the system 20 may have any combination of these components. For example, an embodiment of the system 20 may have only one of the first light detector 24, the second light detector 53 or the third light detector 63. Another embodiment of the system 20 may have the first light detector 24 and the second light detector 53 and may not have the third light detector 63. Yet another embodiment of the system 20 may have the first light detector 24 and the third light detector 63 and may not have the second light detector 53. Moreover, an embodiment of the system 20 may have the second light detector 53 and the third light detector 63 and may not have the first light detector 24.

As shown in FIG. 4, an embodiment of the system 20 may have all three of the first additional light detectors 44, 54, 64. However, embodiments of the system 20 may have any combination of these components. For example, an embodiment of the system 20 may not have any of the first additional light detectors 44, 54, 64. Another embodiment of the system 20 may have only one of the first additional light detectors 44, 54, 64. Yet another embodiment of the system 20 may have only two of the first additional light detectors 44, 54, 64.

As shown in FIG. 4, an embodiment of the system 20 may have all three of the second additional light detectors 45, 55, 65. However, embodiments of the system 20 may have any combination of these components. For example, an embodiment of the system 20 may not have any of the second additional light detectors 45, 55, 65. Another embodiment of the system 20 may have only one of the second additional light detectors 45, 55, 65. Yet another embodiment of the system 20 may have only two of the second additional light detectors 45, 55, 65.

FIG. 5 generally illustrates an embodiment of the system 20 for using the LED 22 to identify the presence of the material 25 in the gas and/or the fluid 26 and/or to determine properties of the material 25. The first light detector 24 may be located adjacent to the second side 32 of the chamber 30 as previously set forth. The first light detector 24 is depicted in FIG. 5 as being located at least partially within the chamber 30. However, the first light detector 24 may be located in a compartment in the second side 32 of the chamber 30, such as the second compartment 34.

The first light detector 24 may be movable with respect to the chamber 30. The first light detector 24 may move from a first position adjacent to the second side 32 of the chamber 30 to a second position adjacent to the second side 32 of the chamber 30. Accordingly, the first light detector 24 may be moved closer to the LED 22, farther away from the LED 22, to a different angle relative to the LED 22, and/or the like. Such movement of the first light detector 24 may enable the light emitted from the LED 22 to travel through less of the gas and/or the fluid 26 before reaching the first light detector 24, through more of the gas and/or the fluid 26 before reaching the first light detector 24, and/or at a different angle through the gas and/or fluid to reach the first light detector 24.

The system 20 may have a moving means 70 which may be activated and/or may be controlled by the microprocessor 90 to move the first light detector 24. The moving means 70 may be, for example, a cable connected to the first light detector 24, a platform mechanically connected to the first light detector 24 so that movement of the platform moves the first light detector 24, an extension which connects the chamber 30 to the first light detector 24 so that movement of the extension moves the first light detector 24, and/or the like. The present invention is not limited to a specific embodiment of the moving means 70, and the moving means 70 may be any component of the system 20 which moves the first light detector 24 from a first position adjacent to the second side 32 of the chamber 30 to a second position adjacent to the second side 32 of the chamber 30.

Movement of the first light detector 24 along the second side 32 of the chamber 30 may enable determination of the properties of the material 25. For example, if the first light detector 24 has a first position 71 directly across the chamber 30 from the LED 22, the amount of light detected by the third light detector 63 relative to the amount of the light emitted by the LED 22 may indicate light transmission of the material 25. As another example, the first light detector 24 may be moved to a second position 72 which may be a first distance 81 from the point directly across the chamber 30 from the LED 22. Then, the first light detector 24 may be moved to a third position which may be a second distance 82 from the point directly across the chamber 30 from the LED 22. The amount of light detected at the first distance and/or the amount of light detected at the second distance may indicate the refractive index and/or the light transmission of the material.

FIG. 6 generally illustrates an embodiment of the system 20 for using the LED 22 to identify the presence of the material 25 in the gas and/or the fluid 26 and/or to determine properties of the material 25. The system 20 may have a first light detector 101, a second light detector 102, a third light detector 103, a fourth light detector 104 and/or a fifth light detector 105 (collectively hereafter "the light detectors 101-105"). Each of the light detectors 101-105 is depicted in FIG. 6 as being located at least partially within the chamber 30. However, one or more of the light detectors 101-105 may be located in a compartment in the second side 32 of the chamber 30, such as the second compartment 34, for example.

Each of the light detectors 101-105 may be located at a different location of the second side 32 of the chamber. Each of the light detectors 101-105 may be, for example, a light intensity detector, a photodiode, a phototransistor and/or other like detector that may output a signal as a function of light intensity detected. In an embodiment, the signal may be a current and/or a voltage. The present invention is not limited to a specific embodiment of the light detectors 101-105 or the signals. Each of the light detectors 101-105 may be any detector which measures an intensity of light known to one having ordinary skill in the art, and the signal may be any means of indicating the light intensity detected known to one having ordinary skill in the art. The system 20 may have any number of light detectors adjacent to the second side 32 of the chamber 30, and the present invention may have any number of light detectors adjacent to the second side 32 of the chamber 30.

As shown in FIG. 7, the microprocessor 90 may be communicatively connected to the light detectors 101-105. The microprocessor 90 may use measurements from each of the light detectors 101-105 and the position of each of the light detectors 101-105 to determine properties of the material 25, such as, for example, the refractive index of the material 25, the light transmission of the material 25 and/or the like.

FIG. 7 generally illustrates an embodiment of the system 20 for using the LED 22 to identify the presence of the material 25 in the gas and/or the fluid 26 and/or to determine properties of the material 25. As previously set forth, one or more of the LED 22, the first light detector 24, the second light detector 53, the third light detector 63, the first additional light detectors 44, 54, 64, the second additional light detectors 45, 55, 65, and the light detectors 101-105 may be electrically connected to the microprocessor 90. In another embodiment, one or more of the LED 22, the first light detector 24, the second light detector 53, the third light detector 63, the first additional light detectors 44, 54, 64, the second additional light detectors 45, 55, 65, and the light detectors 101-105 may wirelessly transmit signals to the microprocessor 50 using a wireless connection.

The signals may indicate the light intensity detected by the corresponding light detector, and/or the microprocessor 90 may process the signals to identify the absence or the presence of the material 25 in the gas and/or the fluid 26. The microprocessor 90 may process the signals to determine properties of the material 25, such as, for example, light reflection, light refraction, light transmission, light diffraction, light interference, light diffusion, light collimation, light absorption and/or light focusing of the material 25. The microprocessor 90 may be electrically connected to a display screen 91 which may visually indicate the absence, the presence and/or the properties of the material 25.

The microprocessor 90 may continuously monitor the absence, the presence and/or the properties of the material 25. As a result, the system 20 may enable real-time monitoring of the absence, the presence and/or the properties of the material 25. The microprocessor 90 may time-stamp the signals received and/or the absence, the presence and/or the properties of the material 25. As a result, information regarding the absence, the presence and/or the properties of the material 25 may be retrieved for a specific time and/or a specific time period. Further, a chart of the absence, the presence and/or the properties of the material 25 as a function of time may be generated. Moreover, based on the real-time monitoring of the absence, the presence and/or the properties of the material 25, the microprocessor 90 may automatically generate a response, such as, for example, an email alert, a text message alert, a pre-recorded voicemail and/or the like.

An input means 92 may be electrically connected and/or wirelessly connected to the microprocessor 90. The input means 92 may be, for example, a keyboard, a mouse, a touchscreen, a joystick, a microphone and/or the like. The present invention is not limited to a specific embodiment of the input means 92. The input means 92 may enable a user of the system 20 to obtain the absence, the presence and/or the properties of the material 25. For example, the user may use the input means 92 to input a selected time, and the microprocessor 90 may use the display screen 91 to display the absence, the presence and/or the properties of the material 25 at the selected time. As another example, the user may use the input means 92 to input a selected position, and the microprocessor 90 may use the display screen to display the light intensity measurements of a light detector located at and/or proximate to the selected position. Moreover, the input means 92 may enable a user of the system 20 to control the moving means 69 and/or the moving means 70.

Accordingly, embodiments of the system 20 may use the LED 22 to identify the presence of the material 25 in the gas and/or the fluid 26 and/or to determine properties of the material 25. The gas and/or the fluid 26 may be located in the chamber 30. The first light detector 24 may be positioned on the opposite side of the chamber 30 relative to the LED 22, the second light detector 53 may be positioned on the same side of the chamber 30 as the LED 22, and/or the third light detector 63 may be positioned inside the chamber 30. The first additional light detectors 44, 54, 64 having a carbon black coating and/or the second additional light detectors 45, 55, 65 having a titanium dioxide coating may enable measurements to be corrected for the effects of temperature.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A system for identifying a presence of a material in a medium wherein the medium is at least one of a gas and a fluid, the system comprising:
    a chamber in which the medium is located wherein the chamber has a first side and a second side wherein the first side is located in an opposite position relative to the second side and further wherein the first side has an aperture;
    an LED to emit light wherein the LED is adjacent to the first side of the chamber wherein the LED is located exterior to the chamber and further wherein the light emitted from the LED transmits into the chamber through the aperture of the first side;
    a first light detector which detects an intensity of the light at a first position on the second side of the chamber wherein the first light detector is adjacent to the second side of the chamber and further wherein the first light detector produces a first signal indicative of the intensity of the light at the first position;
    a second light detector which detects an intensity of the light at a second position on the first side of the chamber wherein the second light detector is adjacent to the first side of the chamber wherein the second light detector is adjacent to the LED wherein the second light detector is located exterior to the chamber and further wherein the second light detector produces a second signal indicative of the intensity of the light at the second position;
    a third light detector which detects an intensity of the light at a third position within the chamber wherein the third light detector is located within the chamber and further wherein the third light detector produces a third signal indicative of the intensity of the light at the third position; and
    a microprocessor communicatively connected to the first light detector, the second light detector and the third light detector wherein the microprocessor processes the first signal, the second signal and the third signal to determine whether the material is present in the medium.

2. The system of claim 1 further comprising:
    a compartment connected to the first side of the chamber wherein the LED and the second light detector are located in the compartment.

3. The system of claim 1 further comprising:
    a compartment connected to the second side of the chamber wherein the first light detector is located in the compartment.

4. The system of claim 1 further comprising:
    a lens on the first side of the chamber wherein the chamber is located on an opposite side of the lens relative to the LED and the second light detector.

5. The system of claim 1 further comprising:
    a lens on the second side of the chamber wherein the lens is located between the first light detector and the chamber.

6. The system of claim 1 further comprising:
    a display screen connected to the microprocessor wherein the display screen visually indicates whether the material is present in the medium.

7. The system of claim 1 further comprising:
    input means connected to the microprocessor wherein user input accepted by the input means indicates a selected time and further wherein the microprocessor responds to the user input by indicating whether the material was present in the medium at the selected time.

8. The system of claim 1 further comprising:
    an additional light detector located adjacent to one of the first light detector, the second light detector and the third light detector wherein the additional light detector has a coating of carbon black wherein the carbon black has a CAS Registry Number of 1333-86-4.

9. The system of claim 1 further comprising:
    an additional light detector located adjacent to one of the first light detector, the second light detector and the third light detector wherein the additional light detector has a coating of titanium dioxide.

10. A method for identifying a presence of a material in a medium wherein the medium is at least one of a gas and a fluid and further wherein the medium is located in a chamber having a first side and a second side wherein the first side is located in an opposite position relative to the second side, the method comprising the steps of:
    emitting light from an LED which is adjacent to the first side of the chamber and which is located exterior to the chamber;
    focusing the light emitted by the LED into the chamber;
    detecting an intensity of the light at a first position on the first side of the chamber wherein the intensity of the light detected at the first position is detected by a light detector adjacent to the LED and exterior to the chamber;
    detecting an intensity of the light at a second position on the second side of the chamber;
    detecting an intensity of the light at a third position within the chamber;
    transmitting the intensity of the light at the first position, the second position and the third position to a microprocessor; and
    comparing the intensity of the light at the first position, the second position and the third position to the light emitted by the LED to determine whether the material is present in the medium wherein the microprocessor determines whether the material is present in the medium.

11. The method of claim 10 further comprising the step of:
    using the intensity of the light at the first position to determine a refractive index of the material wherein the microprocessor determines the refractive index of the material.

12. The method of claim 10 further comprising the step of:
    using the intensity of the light at the first position to determine light transmission of the material wherein the microprocessor determines the light transmission of the material.

13. The method of claim 10 wherein the first position is located on the first side of the chamber.

14. The method of claim 10 wherein the first position is located on the second side of the chamber.

15. The method of claim 10 wherein the first position is located within the chamber.

16. An apparatus for identifying a presence of a material in a medium wherein the medium is at least one of a gas and a fluid, the apparatus comprising:
    a chamber in which the medium is located wherein the chamber has a first side and a second side wherein the first side is located in an opposite position relative to the second side and further wherein the first side has a first aperture and the second side has a second aperture;

an LED to emit light wherein the LED is adjacent to the first side of the chamber and further wherein the LED is located exterior to the chamber;

a lens located within the aperture of the first side wherein the lens focuses the light emitted from the LED into the chamber;

a first light detector which detects an intensity of the light at a first position on the second side of the chamber wherein the first light detector is adjacent to the second side of the chamber and further wherein the light emitted by the LED travels through the second aperture of the second side to the first light detector; and a microprocessor communicatively connected to the first light detector wherein the microprocessor uses the intensity of the light at the first position to determine whether the material is present in the medium.

17. The apparatus of claim 16 further comprising:

a second light detector adjacent to the second side of the chamber wherein the second light detector detects an intensity of the light at a second position on the second side of the chamber and further wherein the second position is a different position relative to the LED than the first position wherein the microprocessor uses the intensity of the light at the first position and the intensity of the light at the second position to determine whether the material is present in the medium.

* * * * *